United States Patent
Bond et al.

[11] 4,030,342
[45] June 21, 1977

[54] ACOUSTIC MICROSCOPE FOR SCANNING AN OBJECT STEREO-OPTICALLY AND WITH DARK FIELD IMAGING

[75] Inventors: Walter L. Bond, Los Altos, Calif.; Cassius C. Cutler, Holmdel, N.J.; Ross A. Lemons, Mountain View, Calif.

[73] Assignee: The Board of Trustees of Leland Stanford Junior University, Stanford, Calif.

[22] Filed: Sept. 18, 1975

[21] Appl. No.: 614,359

[52] U.S. Cl. .............................. 73/67.5 R; 73/67.7
[51] Int. Cl.² ........................................ G01N 29/00
[58] Field of Search .......... 73/67.5 R, 67.5 H, 67.6, 73/67.7, 67.8 R, 67.8 S, 67.9; 340/1 R, 5 MP, 5 H, 8 L

[56] References Cited

UNITED STATES PATENTS

| | | | |
|---|---|---|---|
| 2,164,125 | 6/1939 | Sokoloff | 73/67 |
| 2,565,159 | 8/1951 | Williams | 310/8.7 |
| 2,779,191 | 1/1957 | Willard | 73/67.8 R |
| 2,912,853 | 11/1959 | Hanysz | 73/67.6 |
| 2,919,574 | 1/1960 | Fotland | 73/67.6 |
| 2,938,386 | 5/1960 | Anderson et al. | 73/67.6 |
| 3,013,170 | 12/1961 | Sheldon | 73/67.5 R |
| 3,024,644 | 3/1962 | Fry | 73/67.5 R |
| 3,165,922 | 1/1965 | Worlton | 73/67.7 |
| 3,168,659 | 2/1965 | Bayre et al. | 310/8.3 |
| 3,233,450 | 2/1966 | Fry | 73/67.8 |
| 3,251,219 | 5/1966 | Hertz et al. | 73/67.7 |
| 3,309,655 | 3/1967 | Von Ardenne | 340/15 |
| 3,451,296 | 6/1969 | Alexander | 310/8.1 |
| 3,524,083 | 8/1970 | Last et al. | 310/8.1 |
| 3,533,278 | 10/1970 | Van Valkenburg | 73/67.8 R |
| 3,564,904 | 2/1971 | Brenden et al. | 73/67.5 R |
| 3,587,298 | 6/1971 | Jacobs | 73/67.6 |
| 3,618,696 | 11/1971 | Hurwitz | 340/8 L |
| 3,693,414 | 9/1972 | Soldner | 73/67.9 |
| 3,718,032 | 2/1973 | Gray | 73/67.7 |
| 3,774,717 | 11/1973 | Chodorow | 73/67.7 |
| 3,790,281 | 2/1974 | Kessler | 73/67.5 R |
| 3,795,801 | 3/1974 | Broussaud | 340/5 H |
| 3,832,888 | 9/1974 | Langlois | 73/67.5 R |

OTHER PUBLICATIONS

Lemons, et al., Applied Physics Letters, "Integrated Circuits Viewed With Acoustic Microscope," vol. 25, No. 5, pp. 251–253, Sept., 1974.
Dunn et al., "Journal of Acoustical Society of Amer.," Ultrasonic Absorption Microscope, May, 1959.
Kennedy et al., Practical Improvements and Appl. for Ultrasonic Image Converter, Apr., 1967.
Lawrie et al., Journal of Acoustic Society, "Electronic Imaging of Ultrasonic Fields," 1962.
Ernst, P. J., "Ultransonic Lenses and Transmission Plates," 1945.
Lemons et al., Applied Physics Letters, "Acoustic Microscope–Scanning Version," vol. 24, No. 4, Feb. 2, 1974.
Radio–Electronic Engineering, "Ultrasonic Microscope," Feb., 1953.

*Primary Examiner*—S. Clement Swisher
*Assistant Examiner*—Stephen A. Kreitman
*Attorney, Agent, or Firm*—Flehr, Hohbach, Test, Albritton & Herbert

[57] ABSTRACT

An acoustic microscope for scanning an object stereo-optically and with both dark field and light field imaging. The microscope focuses acoustic waves on a focal point and moves the object in a planar raster pattern through the focal point. The acoustic waves are modulated by the object and displayed on an oscilloscope. The microscope permits the rotation of the object about the focal point so that two, azimuthally displaced images of the object can be obtained. These two images can be observed as one three-dimensional image in a lenticular stereoscope. In addition, the microscope can scan the acoustic waves scattered by the object and display a dark field image of the object.

36 Claims, 10 Drawing Figures

ACOUSTIC MICROSCOPE FOR SCANNING AN OBJECT STEREO-OPTICALLY AND WITH DARK FIELD IMAGING

BACKGROUND OF THE INVENTION

1. Field of the Invention

This invention generally relates to acoustic imaging systems and, more particularly to acoustic microscopy.

2. Description of the Prior Art

Microscopy is the science of using the effect of large magnification to generate usable images of very small objects. In this area of technology light field microscopy develops images from the waves that are either directly transmitted or specularly reflected from the object being observed. In contrast, dark field microscopy develops images from the waves that are scattered by the object into regions outside of the path of the directly transmitted or specularly reflected waves. In dark field microscopy the fine structure of the object is imaged whereas in light field microscopy the course, overall structure is imaged.

U.S. Pat. application Ser. No. 442,782 filed on Feb. 15, 1974, now abandoned, entitled "Scanning Acoustic Microscope," by Mr. Ross Lemons et al. discloses an acoustic microscope for scanning an object with light field imaging. The microscope focuses a high frequency acoustic plane wave with an acoustic lens and scans an object located at the focal plane of the lens. The acoustic waves modulated by the object are recollimated by a second acoustic lens and detected with a piezoelectric transducer. The detected acoustic signal is applied to an oscilloscope that provides a visual display of the acoustic light field image of the object.

Objects and Summary of the Invention

It is the primary object of the present invention to provide a novel method and apparatus that overcomes the limitations and disadvantages of the prior art.

A further object of the present invention is to image objects using scattered acoustic waves. The present invention permits both dark field acoustic microscopy and imaging in the transition zone between the dark and light fields.

An additional object of the present invention is to visualize and record three dimensional, microscopic, image information about the object.

Another object of the present invention is to provide an acoustic miscroscope with greater resolution and capable of generating acoustic images with greater detail.

Still another object of the present invention is to develop acoustic images having higher contrast and greater fine structure detail.

A further object of the present invention is to image objects with both scattered and specularly reflected acoustic waves.

An additional object of the present invention is to compare by addition, subtraction, division and multiplication the reflected and transmitted signals obtained from a scanning acoustic microscope.

These and other objects described herein are achieved by an acoustic microscope for scanning an object stero-optically and with both dark field and light field imaging. The microscope focuses acoustic waves on a focal point and moves the object in a scanning pattern through the focal point. The acoustic waves are modulated by the object, converted into electrical signals, and recorded. The microscope permits rotation of the object about an axis passing through the focal point so that two, angularly displaced images of the object can be obtained. These two images can be stereo-optically combined in a stereo viewer and observed as one three-dimensional image. In addition, the acoustic wave receiver in the microscope can move independently of the object also about an axis passing through the focal point. The microscope can thereby scan the acoustic waves scattered by the object into both the dark field and the transition zone between the dark and light fields.

Additional objects and features of the present invention will appear from the description that follows wherein the preferred embodiments have been set forth in detail in conjunction with the accompanying drawings.

DESCRIPTION OF THE PREFERRED EMBODIMENTS

Figure 1:
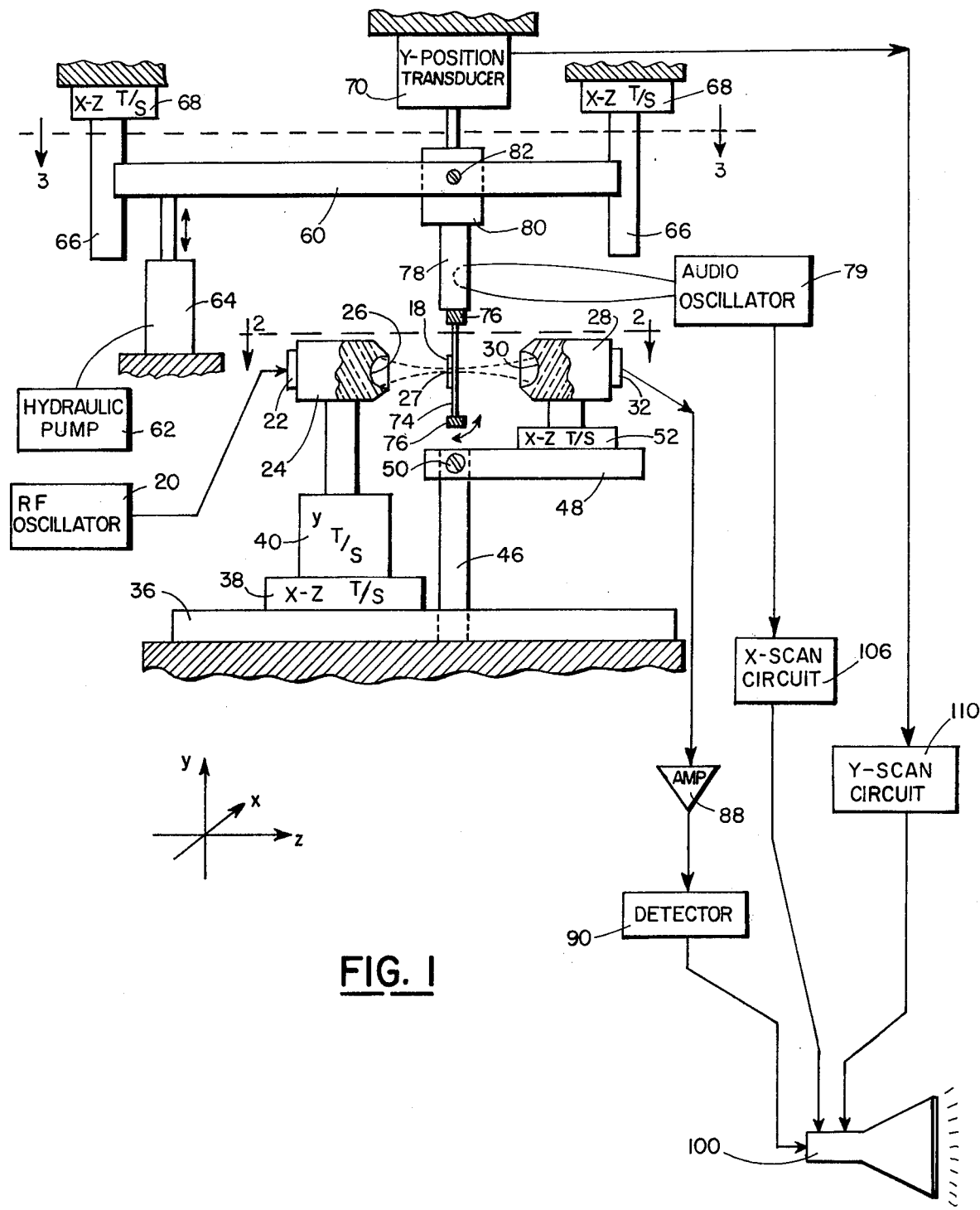
FIG. 1 is a diagrammatic, side elevation partially in section and partially cut away of a scanning acoustic microscope according to the present invention.
Figure 2:
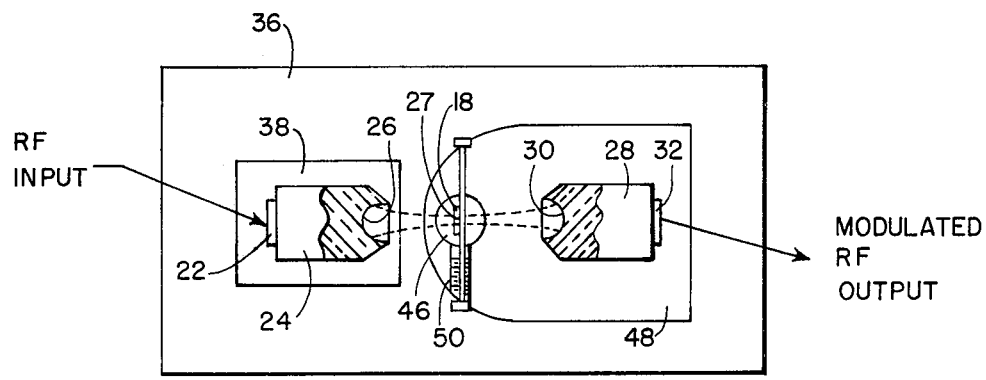
FIG. 2 is a sectional view of the acoustic microscope according to the present invention taken along line 2—2 of FIG. 1.
Figure 3:
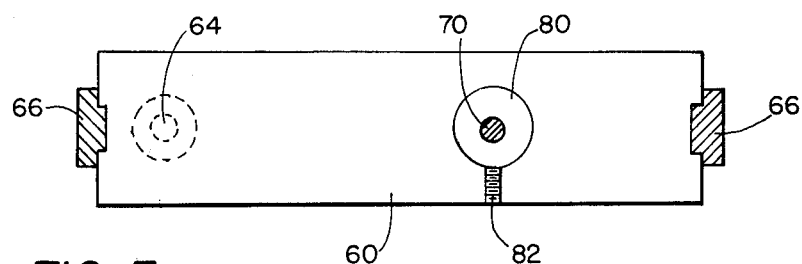
FIG. 3 is a sectional view of the acoustic microscope according to the present invention taken along line 3—3 of FIG. 1.

FIGS. 1, 2 and 3 illustrate a microscope according to the present invention for scanning a relatively movable object 18 with directly transmitted, specularly reflected, and scattered acoustic waves. The microscope includes three subsystems that each cooperate in scanning the object and displaying its acoustic image. The first subsystem generates and focuses the acoustic waves on the object and receives the acoustic waves after interaction with the object. The second subsystem moves the object with respect to the acoustic waves in a predetermined scanning pattern. The third subsystem processes and displays the acoustic image of the object using the signals obtained from the first and second subsystems.

In particular the first subsystem that generates and focuses the acoustic waves on the object and receives the acoustic waves after interaction with the object includes an RF oscillator 20 for generating high frequency signals. The RF oscillator in FIG. 1 is a conventional, variable, fixed frequency oscillator having an output of approximately twenty milliwatts. In one embodiment the RF oscillator operates in the frequency range of 200 to 1500 megahertz. The RF oscillator drives a transducer 22 FIGS. 1 and 2 that converts the high frequency signals from the RF oscillator into acoustic waves. The transducer in the preferred embodiment is a standard zinc oxide RF sputtered thin film. The transmitter is mounted on an acoustic propagating medium that directs the acoustic waves generated by the transducer to an acoustic lens 26. For the purposes of brevity, the propagating medium 24 and the lens 26 will hereinafter be referred to as the acoustic wave transmitter 24.

The acoustic waves propagating from the acoustic wave transmitter 24, FIGS. 1 and 2, are brought to a focal point 27. The acoustic waves thereafter diverge into a second acoustic wave propagating medium 28. The acoustic waves pass into an acoustic lens 30 and are thereby refracted into a beam within the medium. For the purposes of brevity the second propagating medium 28 and the lens 30 will hereinafter be referred to as the acoustic wave receiver 28. The acoustic waves within the acoustic wave receiver thereafter impinge on a transducer 32 and are converted into an electrical signal hereinafter described. The transducer 32 is a conventional zinc oxide RF sputtered film.

The acoustic wave transmitter 24 and receiver 28, FIGS. 1 and 2, can be fabricated from sapphire, YAG, YIG, and fused quartz. In one embodiment of the present invention actually constructed the acoustic lenses 26, 30 had a diameter of 0.4 millimeters, a radius of curvature of 0.39 millimeters and an F number of 1.1. For thicker objects where stereo imaging requires a wider depth of field the lens aperture diameter can be reduced with a small resultant degradation of resolution.

Between the two acoustic lenses 26, 30, FIGS. 1 and 2, there is a fluid acoustic propagating medium (not shown). In the preferred embodiment the gap between the two lenses is filled by a drop of water which is held in place by its own surface tension. It should be appreciated that the gap between the two lenses as illustrated in all of the figures is greatly exaggerated and in one embodiment of the microscope, the gap was approximately 0.7 millimeters. Although water is used in the preferred embodiment, any fluid can be used having an acoustic velocity as small as possible and minimum acoustic wave absorption.

The acoustic wave transmitter 24 and acoustic wave receiver 28 are supported on a stationary platform 36, FIG. 1, that forms the foundation of the microscope. The transmitter is moved with respect to the stationary platform by an X-Z translation stage 38 and a Y-translation stage 40. These translation stages move along the indicated axis and are commercially available.

The acoustic wave receiver 28 is supported above the stationary platform 36 by a post 46, FIG. 1 that is centered so that its major axis passes through the focal point 27 of the microscope. Mounted on the upper end of the post is a rotatable platform 48. The rotatable platform can pivot about the post 46 and can also be locked in place by a set screw 50. The acoustic wave receiver is mounted on the rotatable platform by an X-Z translation stage 52. The combination of the post and rotatable platform permits the acoustic wave receiver to azimuthally rotate about the focal point 27 of the microscope. The translation stages 38, 40, 52 permit the transmitter 24 and receiver 28 to achieve and maintain confocal alignment as the receiver rotates with respect to the transmitter. In other words, the translation stages permit the acoustic lenses 26, 30 to maintain coincident foci for any relative rotational motion between the transmitter and the receiver about the focal point 27.

The second subsystem of the microscope moves the object 18, FIG. 1 in a predetermined scanning or raster pattern with respect to the focal point 27 of the acoustic waves. The second subsystem includes a driven platform 60, FIG. 1 that is elevated in the Y-direction by a hydraulic cylinder 64 connected to a hydraulic pump 62. During each imaging sequence the piston of the hydraulic cylinder continuously elevates the driven platform. The driven platform is maintained in alignment by two vertical guides 66 each attached to a stationary mounting by an X-Z translation stage 68. The two translation stages permit the object 18 to be centered at the focus 27 of the microscope.

The vertical position of the driven platform 60 is measured by a Y-position transducer 70, FIG. 1. The output of the Y-position transducer is an analog, electrical signal indicating the elevation of the object 18 above the focal point of the microscope. In the preferred embodiment the position of the driven platform is measured by a Bimorph transducer which generates an increasing output voltage as the driven platform elevates. The Bimorph transducer is a two plate, sandwich-type, opposite poled, ceramic structure that produces an output signal indicating the amount of deformation to which it is subjected. Bimorph transducers are commercially available from the Vernitron Piezoelectric Division, 232 Forbes Road, Bedford, Ohio 44146.

A second Bimorph transducer provides one dimensional scanning of the object. The object 18 is supported in the gap between the transmitter 24 and the receiver 28 by a Mylar membrane, 74, FIG. 8 supported by a circular ring 76. This ring is attached to one end of the Bimorph. The audio oscillator operates at the resonant frequency of the Bimorph transducer (approximately 100 hertz) and forces the end of the transducer to reciprocally oscillate in response to the varying frequency.

The other end of the Bimorph 78, FIG. 1 is rigidly attached to a selectively rotatable cylinder 80. The cylinder is positioned on the platform 60 so that its major axis passes through the focal point 27 of the microscope and is coaxial with the post 46. The cylinder is rotatable about its major axis and is retained in position by a set screw 82. The purpose of the cylinder is to permit the object 18 to be rotated about an axis passing through the focal point of the microscope.

In the embodiment of the present invention actually constructed, the hydraulic cylinder 64 elevated the driven platform 60 at a smooth and continuous rate. The rate of elevation of the object along the Y-axis was approximately 100 to 1000 times slower than the Bimorph transducer 78 reciprocally moved the object along the Y-axis.

Referring to FIG. 1, the third subsystem of the scanning microscope processes and displays the acoustic image of the object 18 using the signals obtained from the two aforesaid-described subsystems. In the third subsystem the electrical signal obtained from the transducer 32 on the acoustic wave receiver 28 is passed to a heterodyne detector system indicated by amplifier 88. This amplifier-heterodyne system includes a local oscillator (not shown) and a mixer (not shown) that passes its output to a linear IF amplifier (not shown). The output of the amplifier 88 is passed to a detector 90 which, in the preferred embodiment, is a conventional diode detector. The output of the detector 90 is used to modulate the intensity of an oscilloscope 100.

The audio oscillator 79, FIG. 1 that reciprocally drives the object 18 along the X-axis is connected to an X-scan circuit 106. The X-scan circuit includes a magnification control network that adjusts the output voltage of the audio oscillator for use with the oscilloscope 100. The X-scan circuit also includes a phase shift control network that insures that the motion of the Bimorph transducer 78 is synchronized with the scan of the oscilloscope. The output of the X-scan circuit is connected to the oscilloscope 100 and is used to drive the horizontal scan circuit therein.

The Y-position transducer 70, FIG. 1 is connected to a Y-scan circuit 110. The Y-scan circuit includes a single magnification control network that adjusts the output voltage from the position transducer 70 for use by the oscilloscope 100. The output of the Y-scan circuit is passed to the oscilloscope 100 and is used to provide its vertical input.

Operation

In general, the operation of the three microscope subsystems causes the object 18 to be moved past the focal point 27 of the microscope in a raster pattern and generates an acoustic image of the object displayed on the oscilloscope 100. In particular, the RF oscillator 20, FIG. 1 generates a high frequency signal that is converted into acoustic waves by the transducer 22. The acoustic waves propagate through the transmitter 24 and are focused at the focal point 27 by the acoustic lens 26. In FIGS. 1 and 2 the acoustic waves pass through the object 18 in a transmission mode and the physical structure of the object modulates the acoustic beam. The modulated acoustic waves thereafter pass into the acoustic lens 30 where the waves are refracted and propagated in the receiver 28. The acoustic waves are next converted into corresponding electrical output signals by the transducer 32. These corresponding electrical signals are used to modulate the intensity on the oscilloscope 100 after being passed through the heterodyne detector and amplifier system 88 and the detector 90.

During scanning the object 18 is continuously elevated in the Y-direction by the piston of the hydraulic cylinder 64. The Y-directional motion of the object is converted into an electrical signal by the Y-position transducer 70 and the Y-scan circuit 110. The output of the Y-scan circuit provides the vertical input to the oscilloscope 100.

Also during scanning the object 18, FIG. 1, is reciprocally driven along the X-axis by the Bimorph transducer 78 and the audio oscillator 79. The X-directional motion of the object is synchronized with the horizontal scan of the oscilloscope 100 by the X-scan circuit 106. In the embodiment actually constructed the X-directional motion of the object was at least one hundred times faster than the Y-directional motion.

Thus, from the foregoing description it can be appreciated that the object 18 is moved through the focal point 27 of the microscope in a scanning raster pattern and this raster pattern is synchronized with the raster scan of the oscilloscope 100. In addition, as the object is moved through the focal point, the object modulates the acoustic beam in accordance with the transmissivity of the object currently at the focal point. The variations in acoustic transmissivity appear as contrasting light and dark areas on the oscilloscope presentation. Each point on the oscilloscope presentation corresponds to a point on the object because the raster motion pattern of the object is synchronized with the raster scan of the oscilloscope.

Stereoscopic Operation

Figure 4:
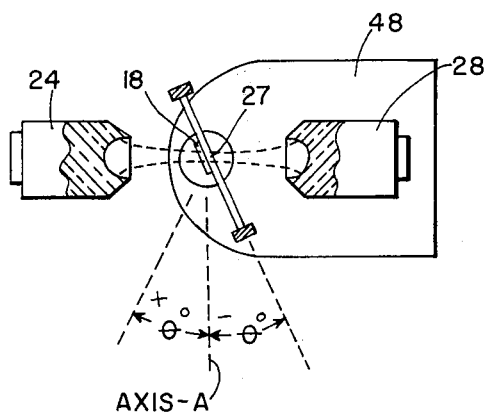
FIG. 4 is a diagrammatic, plan view of the acoustic wave transmitter and receiver of FIG. 2 illustrating the rotation of the object about an axis passing through the focal point of the microscope.
Figure 5:
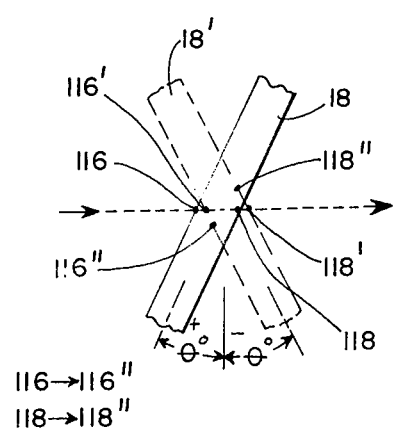
FIG. 5 is a pictorial illustration of a portion of the rotatable object of FIG. 4 illustrating two, angularly displaced images of the object.
Figure 6:
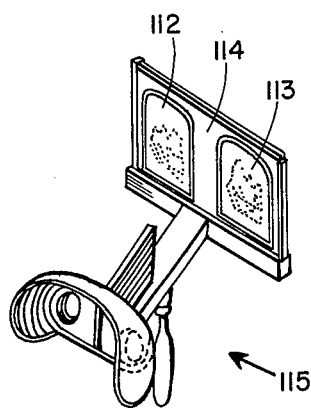
FIG. 6 is a perspective view of a conventional lenticular stereoscope for viewing the two images of the object in three dimensions.

FIGS. 4, 5 and 6 illustrate a method and apparatus for operating the present invention to produce stereo images of the object being scanned. In FIG. 4 the object 18 is rotated counter-clockwise about the focal point 27 for an angle of $-\theta°$ by turning the cylinder 80, FIG. 1 with respect to the platform 60. In the preferred embodiment, the angle $\theta$ is measured from an axis normal to th axis of propagation of the acoustic waves. The acoustic wave transmitter 24 and receiver 28 are maintained in coaxial alignment. An acoustic image of the object 18 at $-\theta°$ is made in the hereinbefore described manner. The image is displayed on the oscilloscope 100, FIG. 1 and a photograph of the image is taken.

Thereafter, the object 18 is rotated clockwise about the focal point 27 to an angle of $+\theta°$. A second acoustic image is generated on the oscilloscope 100 in the same manner and this second image is also photographed.

Referring to FIG. 6, the two photographs 112 and 113 of the two images are mounted on a card 114 in spaced apart relationship. The card is placed in a conventional lenticular stereoscope 115 and viewed in the usual manner. When an observer looks into the stereoscope, he sees the two photographs 112, 113 fused into one image and with a perception of depth analogous to normal three dimensional vision.

FIG. 5 illustrates the geometry of rotating the object 18 $+\theta°$ and $-\theta°$ about the focal point 27. When the object 18 is located at an angle of $+\theta°$, the acoustic beam enters the object at point 116 and leaves the object at point 118. When the object is rotated counter clockwise to an angle of $-\theta°$, the acoustic beam enters the object 18' at point 116' and leaves the object at point 118'. It should be noted that on the object 118' the points 116, 118 have moved to the position 116", 118". The net result is that when the object is rotated from one angular position to another, the same points on the object appear at different positions on the two photographs. When the two photographs are observed through a stereoscope, the angular displacement gives the perception of depth to the observer.

It has been observed during stereo-optic operation of the present invention that when the object 18 has a substantial thickness, better stereo photographs are obtained. The object's thickness enhances the spatial displacement between the two photographs. In other words, if the object is very thin, then there is virtually no displacement between the points 116, 118 and the points 116" and 118" in FIG. 5.

It has also been observed that when the focus or waist of the acoustic beam is held constant across the object, optical distortion in the two photographs is minimized. In order to obtain this constant waist dimension, a wider depth of field is used and the diameter of the aperture is decreased.

In the embodiment of the present invention actually constructed and operated, stereo photographs were obtained at angles of $\theta$ up to 40°.

Dark Field Operation

Figure 7:
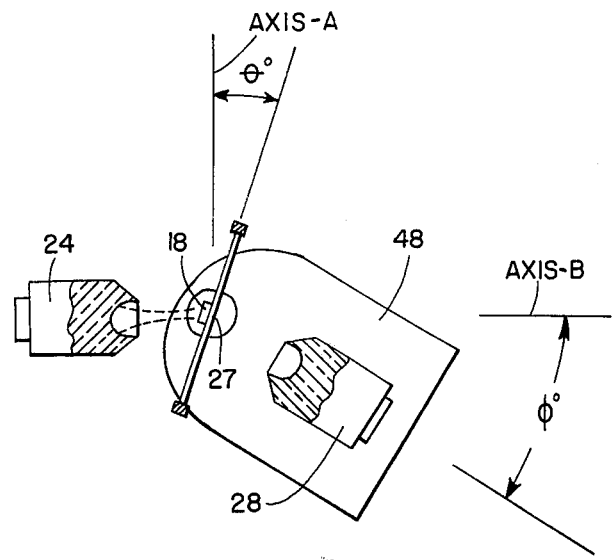
FIG. 7 is a diagrammatic, plan view of the acoustic wave transmitter and receiver of FIG. 2 illustrating the rotation of both the object and the receiver about the focal point.
Figure 8:
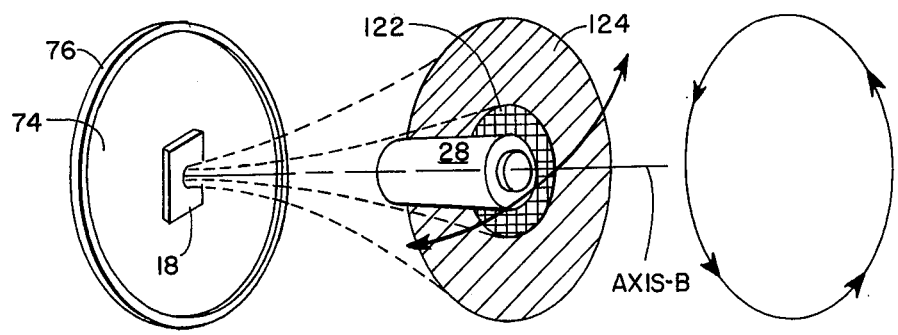
FIG. 8 is a pictorial illustration of the acoustic waves transmitted through the object illustrating the bright field and the dark field.

FIGS. 7 and 8 illustrate the operation of the present invention wherein the scanning microscope records the acoustic waves scattered by the object 18. In those figures axis-B is the axis of propagation of the acoustic waves and is also the longitudinal axis of the acoustic wave transmitter 24. Angle $\phi$ is measured from axis-B to the longitudinal axis of the receiver 28. Angle $\phi$ represents the rotation of the receiver about the focal point 27. Axis A is located in a plane normal to the axis of propagation of the beam and angle $\phi$ is measured from axis A to the plane of the object.

As illustrated in FIG. 1, the object 18 can be rotated about the focal point 27 to any angle $\phi$ by rotating the cylinder 80 with respect to the driven platform 60. The acoustic wave receiver 28 can also be moved to any angle $\phi$ by rotating the platform 48 about the vertical post 46. Either the object or the receiver or both can be independently rotated with respect to the transmitter.

FIG. 8 illustrates in perspective the radiation transmitted through the object 18. The majority of the acoustic waves incident on the object are directly transmitted through the object without scattering. These waves 122 propagate along axis-B without substantial dispersion. In microscopy the area into which these directly transmitted acoustic waves pass is called the light field. There is also a portion of the incident acoustic waves that interact with the object and are scattered at angles outside of or beyond the light field. In microscopy this area 124 is called the dark field.

As hereinbefore described the present invention permits the microscope to scan acoustic radiation within the light field, the dark field and in between. At a position between the light and dark fields the microscope observes both directly transmitted and scattered radiation. The acoustic image thus produced is intermediate in appearance between the normal dark field and the bright field images.

When the microscope is operated in the dark field, the object is scanned in exactly the same manner as in the light field. The object is moved through the acoustic beam in a raster pattern that is synchronized to the raster scan of the oscilloscope 100. The object 18 modulates the acoustic waves passing through its structure and these modulated acoustic waves are used used to vary the intensity of the oscilloscope.

Although the apparatus hereinbefore described and illustrated in FIGS. 1-7 rotates the acoustic wave receiver 28 in the plane of the X and Z axes and about the Y-axis, it is contemplated that the present invention also includes means for moving the acoustic wave receiver throughout the entire solid angle of the dark field 124. The acoustic wave receiver 28 can be rotated about axis-B, FIG. 8 by suitable mechanical staging. Or, in the alternative, the ring 76 can be rotated about axis-B so that the entire solid angle of the dark field can be passed in front of the receiver 28 moving in the X-Z plane.

One reason for observing the object 18 in the dark field is that the acoustic images produced thereby have substantial improvement in resolution. It is well known in both optical and electron microscopy that fine structure tends to scatter radiation predominantly at higher angles. Course structure does not and it is the course structure that is observed in the light field. Thus, in the dark field the scanning microscope can image the finely detailed structure of the object that is otherwise unobservable in the light field 122.

Operation in Reflection

Figure 9:
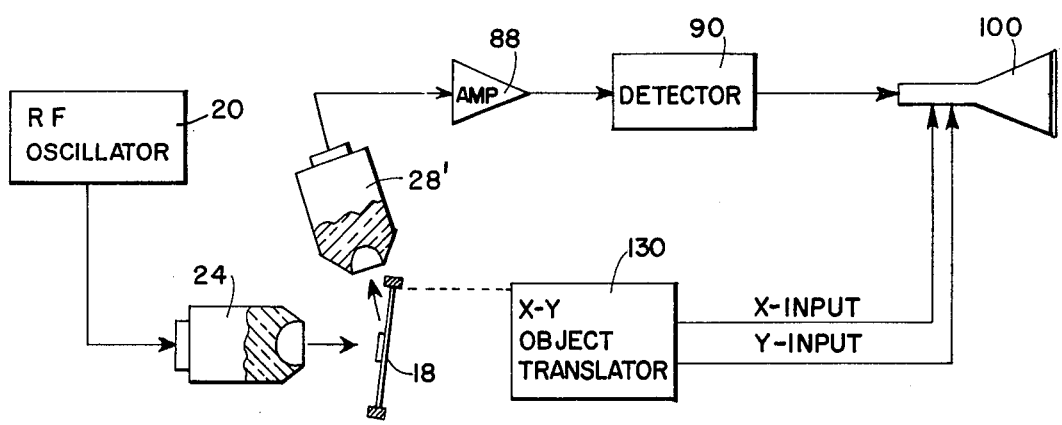
FIG. 9 is a diagrammatic, plan view of the acoustic wave transmitter and receiver of FIG. 2 positioned for scanning specularly reflected and scattered acoustic waves.

FIG. 9 illustrates the operation of the scanning microscope in a reflection mode. The acoustic wave receiver 28' is moved into position to receive reflected acoustic waves by rotating the platform 48, FIG. 1 about the vertical post 46, FIG. 1. The object 18 is rotated into position by turning the cylinder 80, FIG. 1 with respect to the elevatable platform 60.

As hereinbefore described the receiver 28' and the object are independently positionable at any angle $\theta$ or $\phi$, FIG. 7. The receiver 28' can be positioned to receive acoustic waves specularly reflected from the object 18 in accordance with Snell's Law and can also be moved to other angles so that scattered acoustic waves reflected by the object 18 can be received. In a manner analogous to the transmission mode (FIGS. 7 and 8), the scattered radiation can provide information about finer detail in the object than is contained in the specularly reflected acoustic beam.

When the microscope is operated in the reflection mode (FIG. 9), the object is scanned in exactly the same manner as in the transmission mode (FIG. 1). The object is moved in the acoustic beam in a raster pattern that is synchronized to the raster scan of the oscilloscope 100. The object 18 modulates the acoustic waves reflected by its structure and these modulated acoustic waves are used to vary the intensity of the oscilloscope.

Combined Operation

Figure 10:
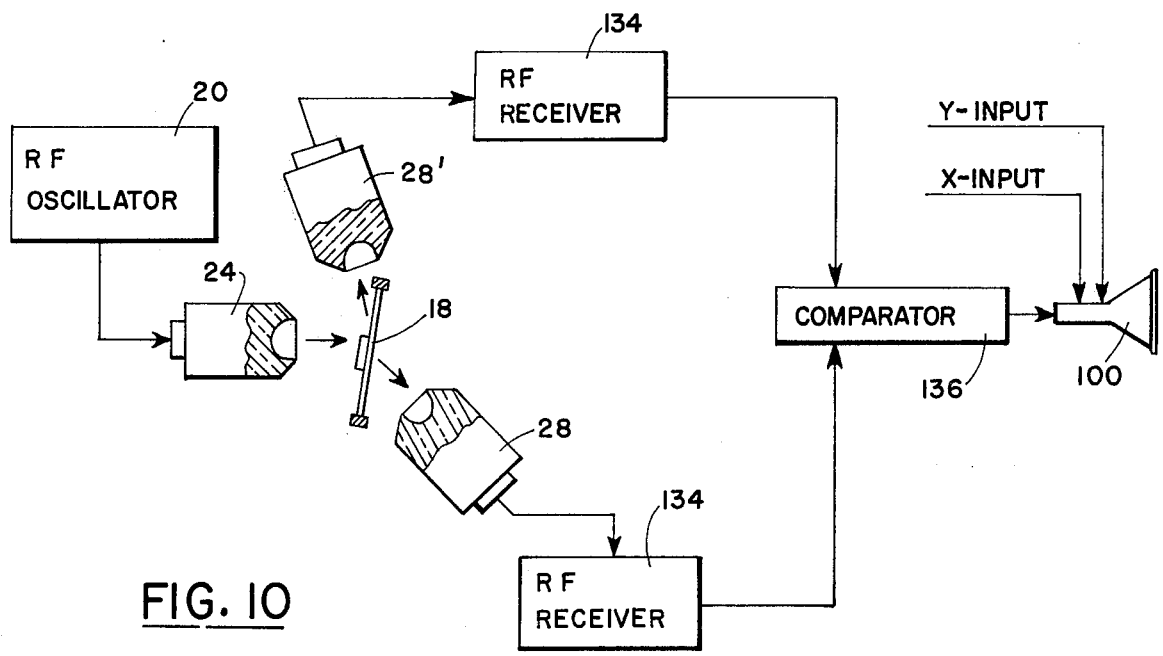
FIG. 10 is a diagrammatic, plan view of an acoustic microscope for scanning both reflected and transmitted acoustic waves and for comparing these reflected and transmitted signals.

FIG. 10 illustrates the operation of the scanning microscope wherein two acoustic wave receivers 28, 28' are used in combination to observe simultaneously the acoustic waves transmitted and reflected by the object. The output of each receiver is connected to an RF receiver 134 which in turn is connected to a comparator 136. Each RF receiver 134 incorporates the amplifier 88, FIG. 1 and the detector 90 hereinbefore described. The comparator can be any circuit that either adds, subtracts, multiplies, or divides two electrical inputs. The output of the comparator is passed to the oscilloscope 100 and modulates the intensity thereof.

The purpose of using a combination of acoustic wave receivers 28, 28' is to provide synchronized acoustic image comparisons between the transmission and reflection modes. The various mathematical operations performed on the receiver signals contrast and amplify the differences between the two operating modes.

It should be noted that all of the embodiments described hereinbefore generate an acoustic image of the object wherein the contrast of the picture corresponds to the modulation of the acoustic waves by the object. It is also contemplated, however, that the present invention also includes means for comparing the phase differences between the electrical signals after conversion of the acoustic as modulated by the object and the electrical signals not modulated by the object. A system for accomplishing such a phase difference measurement is disclosed in U.S. patent application Ser. No. 442,782 entitled "Scanning Acoustic Microscope".

Further, it should be appreciated that the present invention also includes a microscope that moves relative to the object. The object remains stationary and the transmitter and receiver are driven in a raster pattern by mechanical means similar to those described herein. The raster pattern is synchronized to an oscilloscope in the manner hereinbefore described and an acoustic image of the object is generated.

Moreover, although in the preferred embodiments the outputs of the systems illustrated in FIGS. 1, 9 and 10 are connected to an oscilloscope, it is contemplated that the outputs can also be passed to any other suitable information recording apparatus such as a magnetic tape recorder, plotter or digital computer memory.

Although the best mode contemplated for carrying out the present invention has been herein shown and described, it will be apparent the modification and variation may be mead without departing from what is regarded to be the subject matter of the invention.

What is claimed is:

1. An acoustic microscope for imaging an object of interest at a plurality of aspects, comprising:
   a. an acoustic transmitter for generating focused acoustic waves along an axis of propagation and having an acoustic lens at one end thereof for focusing the acoustic waves to a focal point;
   b. an acoustic receiver for receiving along an axis of reception the acoustic waves propagated from the transmitter, said receiver having an acoustic lens at one end thereof for recollimating the received waves and a transducer opposite thereto for converting the recollimated waves into electrical signals;
   c. means for positioning the acoustic lens of the acoustic transmitter and the acoustic lens of the acoustic receiver so that the focal points of each lens are coincident with each other;
   d. means providing relative movement between the object and the microscope in a planar scanning pattern while maintaining the coincident focal points of each lens in the plane of the scanning pattern so that the object of interest modulates the acoustic waves and the electrical signals from the transducer converted therefrom; and
   e. means for rotating the plane of the scanning pattern about an axis passing through the coincident focal points of the lenses while maintaining the coincident focal points of each lens in the plane of the scanning pattern so that the object of interest can be imaged in a plurality of aspects; and
   f. means connected to the transducer for recording the electrical signals corresponding to the acoustic waves modulated by the object of interest.

2. The apparatus of claim 1 wherein the recording means includes means for obtaining a picture of the object wherein the contrast of the picture at predetermined locations corresponds to changes in the modulation of the acoustic waves by the object, said predetermined locations corresponding to the position of the object as determined by the moving means.

3. The apparatus of claim 1 wherein the acoustic wave transmitter operates at a frequency of at least 100 MHz.

4. The apparatus of claim 1 wherein the means providing relative movement in a scanning pattern translates the object through the foci of the acoustic lenses in two mutually perpendicular directions.

5. The apparatus of claim 1 wherein the means providing relative movement in a scanning pattern translates the object in a raster pattern and the recording means includes a CRT display with a raster synchronized with the translation of the object.

6. The apparatus of claim 1 wherein the transmitter and receiver are coaxially disposed and the acoustic waves are transmitted through the object.

7. The apparatus of claim 1 wherein the transmitter and receiver are angularly disposed and the acoustic waves are reflected off of the object.

8. The apparatus of claim 1 wherein the recording means includes means for comparing the phase differences between the electrical signals after conversion of the acoustic waves as modulated by the object and the electrical signals not modulated by the object.

9. The apparaus of claim 1 wherein the relative moving means translates the object with respect to the microscope.

10. The apparatus of claim 1 wherein the relative moving means translates the microscope with respect to the object.

11. A method for stereo-optically imaging an object using an acoustic microscope, comprising the steps of:
   a. propagating acoustic waves in an acoustic wave propagating medium;
   b. focusing the acoustic waves on an object located at the focal point of the microscope, said object being located at an angle $\theta$ measured with respect to an axis normal to the axis of propagation of the acoustic waves;
   c. moving one of either the object at angle $\theta$ or the microscope with respect to the other in a scanning pattern through the focal point of the microscope, thereby modulating the acoustic waves with the object located at angle $\theta$;
   d. displaying a first image of the object corresponding to the acoustic waves modulated by the object;
   e. focusing the acoustic waves on the object located at the focal point of the microscope, said object being located at an angle $\theta'$ measured with respect to an axis normal to the axis of propagation of the acoustic waves;
   f. moving one of either the object at angle $\theta'$ or the microscope with respect to the other in a scanning pattern through the focal point of the microscope, thereby modulating the acoustic waves with the object located at angle $\theta'$;
   g. displaying a second image of the object corresponding to the acoustic waves modulated by the object at angle $\theta'$; and
   h. combining the first and second images in a stereo viewer means so that a stereo-optical image of the object is obtained.

12. The method of claim 11 wherein the absolute values of angle $\theta$ and $\theta'$ are equal.

13. The method of claim 11 wherein the values of angle $\theta$ and $\theta'$ vary between 0° and 45°.

14. The method of claim 11 wherein the steps of modulating the acoustic waves at angles $\theta$ and $\theta'$ include transmitting acoustic waves through the object.

15. The method of claim 11 wherein the steps of modulating the acoustic waves at angles $\theta$ and $\theta'$ include reflecting acoustic waves off of the object.

16. An acoustic microscope for imaging an object of interest with off-axis acoustic waves modulated by the object, comprising:
   a. an acoustic transmitter for generating focused acoustic waves along an axis of propagation and having an acoustic lens at one end thereof for focusing the acoustic waves to a focal point;
   b. an acoustic receiver for receiving along an axis of reception the acoustic waves propagated from the transmitter, said receiver having an acoustic lens at one end thereof for recollimating the received waves and a transducer opposite thereto for converting the recollimated waves into electrical signals;
   c. means for positioning the lens of the acoustic transmitter and the acoustic lens of the acoustic receiver so that the focal points of each lens are coincident with each other;
   d. means providing relative movement between the object and the microscope in a planar scanning pattern while maintaining the coincident focal points of each lens in the plane of the scanning pattern so that the object of interest modulates the acoustic waves and the electrical signals from the transducer converted therefrom;
   e. means providing relative rotational movement between the acoustic receiver and the microscope about a first axis passing through the coincident focal points of the lenses while maintaining the coincident focal points of each lens in the plane of the scanning pattern so that off-axis, acoustic waves from the object of interest are received by the acoustic receiver; and
   f. means connected to the transducer for recording the electrical signals corresponding to the acoustic waves modulated by the object of interest.

17. The apparatus of claim 16 further including means providing relative rotational movement between the object and the microscope about a second axis passing through the coincident focal points of the lenses.

18. The apparatus of claim 17 wherein one of either the object or the microscope rotates with respect to the other in a range of between 0° and 40° with respect to the second coincident focal point axis.

19. The apparatus of claim 17 wherein one of either the acoustic receiver or the microscope moves with respect to the other in a range of between 0° and 40° with respect to the first coincident focal point axis.

20. The apparatus of claim 16 wherein the recording means includes means for obtaining a picture of the object wherein the contrast of the picture at predetermined locations corresponds to changes in the modulation of the acoustic waves. by the object, said predetermined locations corresponding to the position of the object as determined by moving means.

21. The apparatus of claim 16 wherein the acoustic wave transmitter operates at a frequency of at least 100 MH$_z$.

22. The apparatus of claim 11 wherein the means providing relative movement in a scanning pattern translates the object through the foci of the acoustic lenses in two mutually perpendicular directions.

23. The apparatus of claim 11 wherein the means providing relative movement in a scanning pattern translates the object in a raster pattern and the recording means includes a CRT display with a raster synchronized with the translation of the object.

24. The apparatus of claim 16 wherein the recording means includes means for comparing the phase difference between the electrical signals after conversion of the acoustic waves as modulated by the object and the electrical signals not modulated by the object.

25. The apparatus of claim 16 wherein the relative moving means translates the object with respect to the microscope.

26. The apparatus of claim 16 wherein the relative moving means translates the microscope with respect to the object.

27. A method for imaging an object of interest with off-axis acoustic waves using an acoustic microscope, comprising the steps of:
   a. generating focused acoustic waves along an axis of propagation using an acoustic transmitter with an acoustic lens;
   b. receiving the focused acoustic waves from the transmitter along an axis of reception using an acoustic receiver with an acoustic lens;
   c. positioning the acoustic lenses in the acoustic transmitter and receiver so that the focal points of the lenses are coincident;
   d. positioning the transmitter and the receiver so that the respective axes of propagation and reception intersect at an angle $\phi$;
   e. moving one of either the object of interest or the microscope with respect to the other through the focused acoustic waves in a planar scanning pattern so that the object of the interest modulates the acoustic waves;
   f. maintaining the coincident focal points of the lenses in the plane of the scanning pattern for any angle $\phi$ so that off-axis acoustic waves from the object of interest are received by the acoustic receiver;
   g. converting the acoustic waves received by the receiver into corresponding electrical signals; and
   h. recording the electrical signals to obtain an image of the object of interest.

28. The method of claim 27 wherein the angle $\phi$ varies in a range of between 0° and ± 180°.

29. The method of claim 27 further including the step of positioning the object at an angle $\theta$ measured with respect to an axis normal to the axis of propagation of the acoustic waves.

30. The method of claim 27 wherein the step of modulating the acoustic waves with the object includes transmitting acoustic waves through the object.

31. The method of claim 27 wherein the step of modulating the acoustic waves with the object includes reflecting acoustic waves off of the object.

32. A method for comparison imaging an object of interest using an acoustic microscope, comprising the steps of:
   a. generating focused acoustic waves along an axis of propagation using an acoustic transmitter with an acoustic lens;
   b. receiving the focused acoustic waves from the transmitter along a first axis of reception using a first acoustic receiver with a first acoustic lens;
   c. positioning the first receiver for receiving the acoustic waves that are transmitted through the object of interest;
   d. receiving the focused acoustic waves from the transmitter along a second axis of reception using a second receiver with a second acoustic lens;

e. positioning the second receiver for receiving the acoustic waves that are reflected by the object of interest;
f. positioning the acoustic lenses in the acoustic transmitter and the two receivers so that the focal points of the three lenses are coincident;
g. moving one of either the object of interest or the microscope with respect to the other through the focused acoustic waves in a planar scanning pattern so that the object of interest modulates the acoustic waves;
h. maintaining the three coincident focal points of the lenses in the plane of the scanning pattern so that acoustic waves from the object of interest are received by the two acoustic receivers;
i. converting the acoustic waves received by the two receivers into two electrical output signals;
j. comparing the two output signals from the two receivers; and
k. recording the comparison signals to be obtain an image of the object of interest.

33. The method of claim 32 wherein the step of comparing includes adding the output signals together from the first and second receiving means.

34. The method of claim 32 wherein the step of comparing includes subtracting the output signals from the first and second receiving means.

35. The method of claim 32 wherein the step of comparing includes multiplying the output signals together from the first and second receiving means.

36. The method of claim 32 wherein the step of comparing includes dividing the output signals from the first and second receivers.

* * * * *

UNITED STATES PATENT AND TRADEMARK OFFICE
CERTIFICATE OF CORRECTION

PATENT NO. : 4,030,342

DATED : June 21, 1977

INVENTOR(S) : Walter L. Bond, Cassius C. Cutler, Ross A. Lemons

It is certified that error appears in the above-identified patent and that said Letters Patent are hereby corrected as shown below:

IN THE CLAIMS:

Column 14, line 7: delete "receiving means" and insert -- receivers --.

line 10: delete "receiving means" and insert -- receivers --.

line 13: delete "receiving means" and insert -- receivers --.

Signed and Sealed this

Thirteenth Day of September 1977

[SEAL]

Attest:

RUTH C. MASON
Attesting Officer

LUTRELLE F. PARKER
Acting Commissioner of Patents and Trademarks